(12) United States Patent
Deysarkar et al.

(10) Patent No.: US 10,946,112 B1
(45) Date of Patent: Mar. 16, 2021

(54) SYSTEMS AND METHODS FOR THE PRODUCTION OF GELLED SANITIZER COMPOSITIONS UNDER EXTENSIONAL FLOW CONDITIONS

(71) Applicant: PfP Industries, LLC, Houston, TX (US)

(72) Inventors: Asoke Kumar Deysarkar, Houston, TX (US); Michael Joseph Callanan, IV, Houston, TX (US); Robert Ray McDaniel, Cypress, TX (US); Brian James Keola DeCaires, Cypress, TX (US)

(73) Assignee: PfP Industries, LLC, Houston, TX (US)

( * ) Notice: Subject to any disclaimer, the term of this patent is extended or adjusted under 35 U.S.C. 154(b) by 0 days.

(21) Appl. No.: 16/922,738

(22) Filed: Jul. 7, 2020

Related U.S. Application Data

(63) Continuation-in-part of application No. 16/556,566, filed on Aug. 3, 2019, now Pat. No. 10,703,963.

(51) Int. Cl.
| | |
|---|---|
| *A61L 2/18* | (2006.01) |
| *B01J 13/00* | (2006.01) |
| *A61L 2/26* | (2006.01) |
| *A61L 101/02* | (2006.01) |
| *A61L 101/34* | (2006.01) |
| *A61L 101/46* | (2006.01) |
| *C09K 8/80* | (2006.01) |

(52) U.S. Cl.
CPC ................ *A61L 2/186* (2013.01); *A61L 2/26* (2013.01); *B01J 13/0056* (2013.01); *B01J 13/0065* (2013.01); *C09K 8/80* (2013.01); *A61L 2101/02* (2020.08); *A61L 2101/34* (2020.08); *A61L 2101/46* (2020.08)

(58) Field of Classification Search
None
See application file for complete search history.

(56) References Cited

U.S. PATENT DOCUMENTS

| 4,422,947 A | * | 12/1983 | Dorsey | ................... C09K 8/08 |
| | | | | 507/110 |
| 5,052,486 A | * | 10/1991 | Wilson | .................. B01F 3/0861 |
| | | | | 166/308.4 |

(Continued)

*Primary Examiner* — John J Figueroa
(74) *Attorney, Agent, or Firm* — Vorys, Sater, Seymour and Pease LLP (57) ABSTRACT

Methods include producing a gelled sanitizer composition, including preparing a hydrating fluid composition including water and one or more of alcohol and peroxide; preparing a hydratable additive; and combining the hydrating fluid composition and the hydratable additive to produce a gelled composition. Methods also include flowing a hydrating liquid composition in an extensional flow regime through an elongated passageway of an extender, wherein the hydrating liquid composition includes water and a C2-C10 solvent, and a flow rate of the hydrating liquid composition and a diameter of the elongated passageway are sufficient to achieve a Reynolds number of 20,000 or greater; and adding a hydratable additive to the hydrating liquid composition in the elongated passageway to produce a mixture comprising the hydratable additive that is at least partially hydrated.

17 Claims, 2 Drawing Sheets

(56) References Cited

U.S. PATENT DOCUMENTS

| | | | |
|---|---|---|---|
| 6,387,853 B1* | 5/2002 | Dawson | C09K 8/90 |
| | | | 507/209 |
| 2006/0027364 A1* | 2/2006 | Kelly | C09K 8/5758 |
| | | | 166/278 |
| 2007/0173412 A1* | 7/2007 | Allin | C09K 8/512 |
| | | | 507/224 |
| 2008/0261836 A1* | 10/2008 | Filler | C09K 8/34 |
| | | | 507/260 |
| 2012/0273206 A1* | 11/2012 | Zamora | C09K 8/68 |
| | | | 166/308.1 |
| 2013/0150268 A1* | 6/2013 | Oldham | B01F 5/0606 |
| | | | 507/215 |
| 2013/0261032 A1* | 10/2013 | Ladva | C09K 8/487 |
| | | | 507/131 |
| 2014/0364344 A1* | 12/2014 | Weinstein | B01F 3/1271 |
| | | | 507/219 |
| 2014/0364346 A1* | 12/2014 | Weinstein | C09K 8/90 |
| | | | 507/225 |
| 2015/0344767 A1* | 12/2015 | Lei | C08B 11/20 |
| | | | 507/224 |

\* cited by examiner

SYSTEMS AND METHODS FOR THE PRODUCTION OF GELLED SANITIZER COMPOSITIONS UNDER EXTENSIONAL FLOW CONDITIONS

BACKGROUND

Transmission of pathogens by vectors such as surfaces and aerosolized particles is well known by consumers. In the absence of cleaning facilities, due to traveling conditions and/or time constraints, sanitizing products have become a mainstay as an alternative without the need for water and/or drying towels.

Although alcohol and alcohol-containing sanitizers are known to be virucidal and bactericidal, such compositions typically require a base of gelled polymer to aid distribution on skin and surfaces. In addition to viscosifying polymers, sanitizers may contain a number of other additives ranging from additional bactericides to cosmetological additives to minimize skin dryness and irritation.

Current processes to form gelled compositions utilize the conditions that incompletely hydrate and/or shear the polymer, which can result in unsatisfactory products and mechanical issues and clogging during production.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure relates to process methods and systems in which one or more process stages incorporate an extender to enhance mixing and place components in an extensional flow regime. In another aspect, methods disclosed herein include the preparation of gelled polymer compositions, including gelled sanitizer compositions. Methods disclosed herein can be used to produce gelled sanitizer compositions using an extender to increase the efficiency of generating a gelled polymer solution, while minimizing or eliminating polymer chain scission or the formation of partially hydrated polymer byproducts, such as fisheyes.

In yet another aspect, methods disclosed herein are directed to improved polymer gel formation in which a dried polymer is prepared as a slurry within a non-aqueous fluid, such as a humectant or other hydrocarbon. Once formed, polymer slurries increase the efficiency of movement through production by enabling the use of liquid handling techniques (pumps, syringes, etc.) for metered delivery and minimization of exposure to the atmosphere (for increased sanitation). Polymer slurries disclosed herein also enable faster and more complete polymer hydration when combined with a hydrating liquid composition, yielding completely or substantially uniform polymer gels. In some embodiments, polymer hydration processes that begin with polymer slurry formation can minimize the time required for screening a final product through filters or meshes, or obviate the need for screening completely.

In the production of polymer gel compositions, such as those used to formulated gelled sanitizer compositions, the hydration of the constituent polymer(s) is time consuming and, in some cases, can involve planned and unplanned plant shutdown to remove clogs and polymer residue from processing equipment. Comparative processes often involve the hydration of a polymer in water, followed by dilution with a solution of alcohol and other various additives. Hydration processes can include the use of a blender, shear mixer, or educator to agitate polymer into the hydrating fluid. However, hydrating polymer by these techniques is relatively time consuming and can create production problems such as clogging or the formation of partially hydrated polymer particles ("fish eyes").

Specific to gelled sanitizer compositions, polymers must also be compatible with solvents such as alcohols that are often used in varying ratios with water as one of the primary functional components of the sanitizer. In some applications, hydrocarbon solvents are added to a hydratable polymer to disperse the polymer particles prior to hydration. However, for cosmetological applications, methods of polymer hydration that rely on hydrocarbon solvents and emulsifiers are often constrained by health and safety issues. Thus, keeping the sanitizer composition free from contamination and impurities becomes a necessity.

The present disclosure is related to gelled sanitizer compositions and, more particularly, to improved systems and methods of hydrating additives, especially dry or semi-dry (referred to herein as "hydratable") additives, with a hydrating fluid composition to produce polymer gels for use in gelled sanitizer compositions. Hydrating fluid compositions can include premixed solvents that include ethanol, water, and peroxide, which can minimize the time needed for sequential steps needed in conventional sanitizer formulation processes.

Methods disclosed herein are directed to the preparation of gelled polymer compositions from hydratable additives that utilize an "extender" that places the mixtures in extensional flow. Use of extensional flow can reduce the time needed for hydrating polymers to reach peak performance properties, while also minimizing the formation of partially hydrated and truncated polymer byproducts. In some embodiments, a dried polymer is prepared as a slurry in a non-aqueous fluid, such as a humectant, that functions similar to hydrocarbon solvents used in industrial polymer hydration properties and remains compatible with cosmetic formulations.

Methods disclosed herein may eliminate or minimize partially hydrated polymer byproducts, shorten the times required to generate hydrated polymer, introduce additives during polymer hydration such as humectants and other cosmetological components.

In some embodiments, methods of producing gelled sanitizer compositions can include preparing a hydrating fluid composition including water and one or more of alcohol and peroxide; preparing a hydratable additive (alone or as a slurry with a humectant or other additive); and combining the hydrating fluid composition and the hydratable additive in an extender to produce a gelled composition.

The systems and methods disclosed herein are primarily applicable to hydratable additives like high molecular weight polymers that are added to cosmetic and medical use compositions. However, those skilled in the art will readily appreciate that the principles disclosed herein are equally applicable to other industries including, but not limited to, oil and gas exploration and extraction, food production, fertilizer production, paint production, and the like.

Embodiments discussed herein describe improved systems and methods of hydrating additives, especially dry additives, to viscosify and/or form gelled compositions for a number of applications including the formulation of sanitizer compositions. Without being limited by theory, it is believed that there are three flow regimes/mechanisms by which polymers can mix with and be hydrated by a hydrating liquid composition. The first is laminar flow where the only mixing that takes places is between two adjacent layers by diffusion. This diffusion is a slow process and controlled by diffusional coefficient. The second is turbulent flow where two mechanisms are present: diffusion and convective (convection) mixing. Convective mixing is the primary mechanism by which mixing and dissolution takes place. In a turbulent regime flow, not only convective mixing takes place, but also diffusion mixing between the layers but with an order of magnitude difference between the two.

The third is extensional flow, which has three mechanisms of mixing: diffusion, convective mixing (very little), and polymer stretching. Because of the high flow rate and small diameter flow path needed to achieve extensional flow, the polymers within a hydratable additive are immediately stretched when exposed to a hydrating liquid composition, which allows for flash hydration of the polymer. This ability to flash hydrate is the result of the combination of the polymer stretching, high energy in the form of fluid velocity but with a substantial absence (preferably complete absence) of turbulence and therefore maximizes structure development of the polymer.

Equipment capable of creating extensional flow conditions (referred to herein as an "extender") allows the hydratable polymers to maximize viscosity and structure development, while minimizing the polymer structure's susceptibility to shear degradation. Methods disclosed herein utilize an extender in mixing (blending) a hydrating liquid composition and a hydratable additive. The extender has a design that causes the hydrating liquid composition to flow through an elongated passageway at a high flow rate to achieve an extensional flow regime at which point the hydratable additive is added to the hydrating liquid. As used herein, the term "extensional flow regime" refers to a flow regime characterized by high momentum diffusion, low momentum convection, and polymer stretching. The extensional flow regime is achieved by the synergistic combination of (a) a high flow rate through the elongated passageway of the extender and (b) a size and shape of the elongated passageway to achieve a Reynolds number (e.g., 20,000 or greater) through the passageway with little to no turbulence or eddies. Such flow rates with viscous fluids are associate with turbulent flow, which produces significant eddies. In contrast, the inlet, elongated passageway, and outlet of the extender are designed to achieve little to no turbulence or eddies as high flow rates.

In some embodiments, the elongated passageway may be designed without or otherwise not including any moving parts that might inadvertently cause shear. Without being bound by theory or mechanism, it is believed that contacting a hydratable additive such as a polymer and hydrating liquid composition in such a manner causes the individual polymer molecules to be wetted and then begin structure development. The smooth, extensional flow regime helps achieve elongation and unfolding of the polymer structure with a minimum of damage or scission (e.g., shortening of the polymer chain) that hydrates more readily.

The extender design then changes to maintain extensional flow but at a lower flow rate than in elongated passageway so that the fluid exiting the extender can be further processed without inducing high shear degradation. Upon leaving the extender, the hydratable additive will be at least partially hydrated and its structure development will have commenced, if not having already been substantially completed. If needed, further processing can include further mixing of the fluid under low shear conditions ($\pm 400$ sec$^{-1}$) to substantially or fully develop the hydrated structure of the hydratable additive (e.g., achieving 85% to 100% of peak viscosity). Because the polymer structure is elongated and unfolded by the mixing and flow conditions in the extender, the time for such further processing and hydration is minimized.

Unless otherwise specified, viscosity is measured using a commercially-available viscometer, such as an Ofite 900 Viscometer. Hydration rate data related to viscosity can be obtained by comparing samples prepared using the extender designs described herein and connected to a conventional hydration tank with samples that are hydrated for the same amount of time but using a lab mixer. In one example, the total amount of mixing time for each sample was 13 seconds before being placed on the viscometer to record the viscosity build-up. In this example, the viscometer was an Ofite 900 Viscometer which was used to record a 300 RPM reading (511 sec$^{-1}$) at 80° F. Readings were taken at 30 seconds, 1, 2, 3 and 5 minutes. Tests were run at a polymer loading of 24 ppt (same polymer was used in both tests). The results are shown below in Table 1:

TABLE 1

| | | Viscosity (cps) | | | | |
|---|---|---|---|---|---|---|
| Sample | Hydration Equipment | 30 sec. | 1 min. | 2 min. | 3 min. | 5 min. |
| 1$^{st}$ Method | Presently Disclosed Extender @ 123 gpm | 12.9 | 17.1 | 28.5 | 33.0 | 33.5 |
| 2$^{nd}$ Method | Lab Mixer @ 1250 RPM | 5.2 | 8 | 14.8 | 21.3 | 24.1 |

As used herein, the term "peak viscosity" refers to the viscosity of a sample when the viscosity is changing by less than 5% over 30 minutes with continuous low shear mixing. A viscosity ($\eta_m$) with X % of the peak viscosity ($\eta_p$) is calculated as $100-((\eta_p-\eta_m)/\eta_p)*100)\geq X$. As used herein, the term "substantially hydrated" refers to a viscosity within 85% of peak viscosity.

One or more of the presently disclosed methods can include flowing a hydrating liquid composition in a extensional flow regime where the flow rate and dimensions of the elongated passageway are chosen to achieve a Reynolds number for the hydrating fluid passing through the elongated passageway of 20,000 or greater (e.g., 50,000, 75,000, 100,000 to 800,000, or 250,000 to 750,000, or 400,000 to 600,000). A hydratable additive may then be added to the hydrating liquid composition in the elongated passageway, such that the hydratable additive becomes at least partially elongated while passing through the elongate passageway, and thereby producing a mixture comprising an at least partially hydrated hydratable additive. The flow rate and dimension of the elongated passageway can be any suitable values to achieve said Reynolds number. By way of non-limiting example, the volumetric flow rate of the hydrating fluid through the elongated passageway may be at least 50 gallons per minute (gpm) (0.19 m³/min) (e.g., 50 gpm to 200 gpm (0.76 m³/min), or 75 gpm (0.28 m³/min) to 175 gpm (0.66 m³/min), or 100 gpm (0.38 m³/min) to 150 gpm (0.57 m³/min)). By way of another nonlimiting example, the diameter of the elongated passageway at its narrowest may be 45 mm or less (e.g., 10 mm to 45 mm, or 10 mm to 30 mm, or 15 mm to 20 mm). By way of yet another nonlimiting example, using water as the hydrating fluid, with a volumetric flow rate of 115 gpm through the elongated passageway, and a diameter of the elongated passageway at its narrowest of 19 mm yields a Reynolds number of about 500,000.

The viscosity of the mixture within 5 minutes (e.g., 10 seconds to 5 minutes, or 30 seconds to 2 minutes, or 1 minute to 3 minutes, or 2 minutes to 5 minutes) of exiting the elongated passageway may be within 50% of the peak viscosity (e.g., within 50% to 100%, or 50% to 75%, or 60% to 80%, or 75% to 90%, or 80% to 95%, or 80% to 100% of the peak viscosity). As provided in Table 1 above, using the extender described herein can result in reaching 50% of Peak Viscosity in less than 1 minute and 85% of Peak Viscosity in 2 minutes.

The methods of the present disclosure can further include conveying the mixture from the extender to a vessel (e.g., a hydration tank) while in the extensional flow regime and low shear mixing of the mixture within the vessel. At higher hydratable additive concentrations (e.g., 3 wt % or greater), the mixture exiting the extender may be diluted with additional hydrating liquid composition or an alcohol (e.g., by introduction into the vessel containing additional hydrating liquid, or by mixing with additional hydrating liquid composition in downstream mixing equipment).

Figure 1:
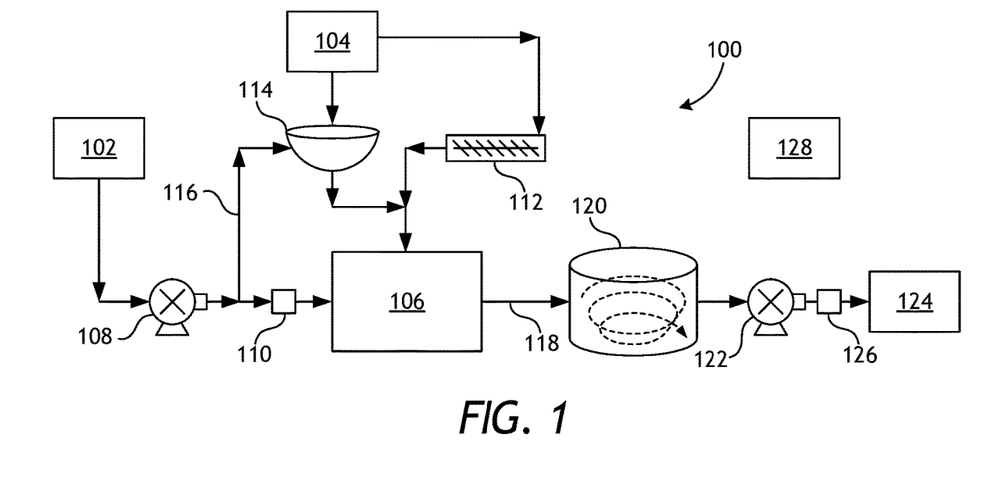
FIG. 1 is a diagram of an example blending system that may incorporate one or more principles of the present disclosure.

By way of nonlimiting example, FIG. 1 is a schematic flowchart diagram of an example blending system 100 that may incorporate one or more principles of the present disclosure. The blending system 100 may be configured to produce a mixture comprising a hydrated polymer, such as a polymer gel, that may be incorporated into a gelled sanitizing composition. The mixture may be blended to a predetermined concentration and diluted depending on formulation requirements. While blending system 100 is presented as an example embodiment for producing gelled compositions in accordance with the present disclosure, modifications are possible. It is also noted that it is desirable that blending system 100 and all equipment that handles gelled sanitizer compositions be free from contamination with microorganisms and surface biofouling.

As illustrated, the blending system 100 includes a hydrating liquid composition 102, a hydratable additive 104, and a mixing device 106 that receives and mixes (blends) the hydratable additive 104 with the hydrating liquid composition 102. In some embodiments, hydratable additive 104 can be supplied as a dry powder or a slurried polymer mixture with a non-aqueous fluid, such as a humectant or other cosmetically acceptable additive.

The hydrating liquid composition 102 may include any aqueous fluid, such as water or a solution comprising water and one or more alcohols. In some embodiments, the hydrating liquid composition 102 can include a mixture of microorganism-free water and any suitable concentration and/or mixture of solvents, salts, or buffers.

The blending system 100 may also include a first or "mixing" pump 108 that conveys (pumps) the hydrating liquid composition 102 to the mixing device 106. The mixing pump 108 may be, for example, a centrifugal pump. In some embodiments, a flow meter 110 may be placed inline before or after the mixing pump 108 to measure the amount of the hydrating liquid composition 102 that is provided to the mixing device 106. As will be appreciated, this may help determine how much hydratable additive 104 must be introduced into the mixing device 106 to meet predetermined concentrations. In some embodiments, for example, the mixing pump 108 may be operated to provide about 400 gallons per minute (gpm) of the hydrating liquid composition 102 through the mixing device 106.

The hydratable additive 104 may be in the form of a powder, fine granules, or a liquid (e.g., a concentration, a suspension, an emulsion, or a slurry). Suitable materials for the hydratable additive 104 include, but are not limited to, polymers, personal care additives, and the like, and any combination thereof. In at least one embodiment, the hydratable additive comprises a polymer suspended in a fluid (e.g., suspended in a hydrocarbon or suspended as an emulsion).

In some embodiments, the hydratable additive 104 includes one or more polymers, such as a polyacrylamide. The extensional flow generated by the extender 202 tends to keep the polymer structure of the hydratable additive 104 more intact, and tends to stretch the polymer without breaking it, thus improving its shear resistance and dynamic proppant transport capability. The mixing device 200 (FIG. 2) may be able to produce a flow of the hydrating fluid 102 with a minimum amount of wasted energy in the form of turbulence, and the hydratable additive 104 (e.g., polymer) is added to this stream. This allows the hydratable additive 104 to be wetted and then begin its structure development. The smooth, extensional flow pattern helps achieve elongation and unfolding of the polymer structure with a minimum of damage (e.g., shortening of the polymer chain). The downstream hydration tank 120 (FIG. 1) may also help improve shear resistance and dynamic proppant transport capability in that it may keep the hydratable additive 104, which is now partially hydrated, in a constant but controlled movement (e.g., spiral flow). This step may complete the stretching of the polymer chains and maximize the area that the polymer structure covers. Hydration tank 120 can also be used to achieve uniform distribution of a hydrated gel and other added components, such as water, alcohol, peroxide, etc. Combining these two blending steps may complete the structural development process. Maximizing the polymer concentration that is reached using this process allows the mixing device 106, 200 (FIGS. 1 and 2, respectively) to support a relatively high polymer concentration and high injection rates through the downstream processing equipment 124 (FIG. 1).

The hydratable additive 104 may be stored in a local hopper, bin, or storage trailer, for example, and may be provided to the mixing device 106 in a variety of ways. To ensure that the hydratable additive 104 freely flows from the storage hopper or trailer, a pneumatic vibrator may run intermittently, and humidity from atmospheric air may be controlled via one or more desiccant filters. In one or more embodiments, as illustrated, the hydratable additive 104 may be fed to an auger 112 that delivers the hydratable additive 104 directly into the mixing device 106. The auger 112 may be operated and otherwise configured to meter a predetermined flow of the hydratable additive 104 into the mixing device 106 to proportionately match the flow of the hydrating liquid composition 102 entering the mixing device 106.

In other embodiments, however, the hydratable additive 104 may be pre-wetted in a wetting chamber 114 prior to being introduced into the mixing device 106. In such embodiments, a portion of the hydrating liquid composition 102 may be pumped through a liquid feed line 116 and into the wetting chamber 114. The hydratable additive 104 may be introduced into the wetting chamber 114 to mix with the portion of the hydrating liquid composition 102 and thereby form a pre-wetted and partially hydrated fluid that is conveyed to the mixing device 106. The wetting container 114 may be, for example, a container, a vessel, a bowl or any type of receptacle suitable for pre-mixing the hydratable additive 104 with the portion of the hydrating liquid composition 102. In some embodiments, the hydratable additive 104 may be metered into the wetting container 114 at a rate between about 7 pounds per minute (lbs/min) and about 30 lbs/min. The wetting chamber 114 is most desirable when using fast hydrating polymers because it allows for a higher amount of dry powder to be added without the development of gel balls or fish eyes.

In pre-wetting, only a small amount of hydrating liquid composition 102 is added to the wetting chamber 114. Preferably, the amount of hydrating liquid composition 102 and hydratable additive 104 are so that the concentration of hydratable additive 104 is at least 5 times (e.g., 5 times to 100 times, or 10 times to 75 times, or 20 times to 50 times) the concentration of the hydratable additive 104 in the mixture 118 described below.

The hydratable additive 104 or the pre-wetted hydratable additive 104 may be thoroughly mixed with the hydrating liquid composition 102 within the mixing device 106, which discharges a concentrated mixture 118 of partially or completely hydrated material. In some embodiments, as described in more detail below, the mixing device 106 may include or otherwise incorporate an extender (not shown), which may perform three primary functions: 1) to provide the motive flow to introduce the hydratable additive 104 into the mixing device 106, 2) to impart energy to the mixture to quickly hydrate the hydratable additive 104 without creating clumps or fish eyes, and 3) to separate and extend the polymer molecules in order to yield more structural benefit and exposure for hydration, thereby promoting very rapid hydration. The geometry of the extender may be optimized to ensure that the flow of the hydrating liquid composition 102 smoothly converges to prevent splashing (eddies) where the hydratable additive 104 is introduced into a jet of hydrating liquid composition 102.

In embodiments, the hydratable additive 104 can be a polymer slurry prepared by combining a polymer with a humectant or other non-aqueous solvent. For example, wetting chamber 114 can be modified (or an additional chamber can be added) to mix a polymer with a humectant to form a slurry 118 that is then conveyed to mixing device 116, where the polymer slurry is mixed with the hydrating liquid composition 102.

In the mixture 118, the hydratable additive may be present in a slurry at a percent by weight (wt %) of a slurry at up to 5 wt %, 10 wt %, or 20 wt % in some embodiments. In some embodiments, the hydratable additive may be present at a wt % ranging from 0.1 wt % to 25 wt %.

The resulting mixture 118 can be a) injected directly into a dilution stream or downstream equipment 124 or tubulars (not shown) or b) conveyed into a hydration tank 120 used to further hydrate (if needed) and temporarily store the mixture 118. In some embodiments, the resulting mixture 118 may be received at a suction manifold in fluid communication with one or both of the hydration tank 120 and the downstream equipment 124. In at least one embodiment, the suction manifold may include a plurality of suction lines (e.g., four or more). As mentioned below, the downstream equipment 124 may comprise, for example, a blender. In such embodiments, suction forces generated by the blender may draw the mixture 118 into and through the manifold, thus resulting in zero head pressure downstream of the mixing device 106. Moreover, when not using the hydration tank, the time from contacting the hydrating liquid composition and hydratable additive in the extender to introducing the resultant mixture into a downstream processing equipment or dilution stream may be 1 minute or less (e.g., immediate to 1 minute, 1 second to 45 seconds, or 5 seconds to 30 seconds).

In some embodiments, the hydration tank 120 may comprise a circular, cylindrical structure. In such embodiments, the mixture 118 may be injected (introduced) into the hydration tank 120 at an angle tangent to the inner sidewall of the hydration tank 120, which induces swirl to the mixture 118 as it enters the hydration tank 120. The swirling flow may provide enough movement in the hydration tank 120 to keep any remaining hydratable additive 104 suspended within the hydrating liquid composition 102 until all the hydratable additive 104 is sufficiently hydrated. This may prove advantageous if the hydratable additive 104 used in the process is a slow hydrating material, and it may also help to maintain homogeneity within the hydration tank 120 while blending.

Residence time in the hydration tank 120 will vary, depending on the hydration time of the hydratable additive 104 and the targeted concentration of the polymer after dilution. In at least one embodiment, the mixture 118 may reside within the hydration tank 120 between 1 and 5 minutes, but could alternatively reside within the hydration tank 120 for a time period that is shorter or longer than 1 to 5 minutes, without departing from the scope of the disclosure, and depending on the hydration requirements of the hydratable additive 104. The fluid level within the hydration tank 120 may be adjusted to increase or decrease the residence time. For example, if a hydratable additive 104 having a slow hydration time is used, the residence time in the hydration tank 120 can be extended by increasing the fluid level. The fluid level within the hydration tank 120 may be maintained through operation of the mixing pump 108, and when associated sensors and controls determine that the fluid level is running high or low, the mixing pump 108 may slow down or speed up to adjust the fluid level.

In some embodiments, downstream equipment 124 can be used to dilute mixture 118 containing the hydrated gel composition with an alcohol or other solvent to form a final gelled sanitizer composition. In some embodiments, the gelled sanitizer composition can include a percent by weight (wt %) of polymer of up to 3 wt %, 5 wt %, or 7.5 wt % in some embodiments. In some embodiments, the hydratable additive may be present at a wt % ranging from 0.1 wt % to 3 wt %.

In some embodiments, the blending system 100 may be fully or partially automated. In such embodiments, the blending system 100 may include a control system 128 used to regulate, monitor, and maintain efficient operation of the blending system 100. The control system 128 may be in communication (either wired or wirelessly) with various components of the blending system 100. The mixing and discharge pumps 108, 122, for example, may be communicably coupled to the control system 128, which may monitor and regulate the flow rate of each pump 108, 122 to ensure that the fluid level within the hydration tank 120 is maintained at a proper level. The control system 128 may also regulate the feed rate of the hydratable additive 104 to ensure that the concentration of the hydratable additive 104 in the mixture 118 is accurate. If the mixing rate increases or decreases to adjust fluid level within the hydration tank 120, for instance, the feed rate of the hydratable additive 104 may also be adjusted autonomously by the control system 128.

Figure 2:
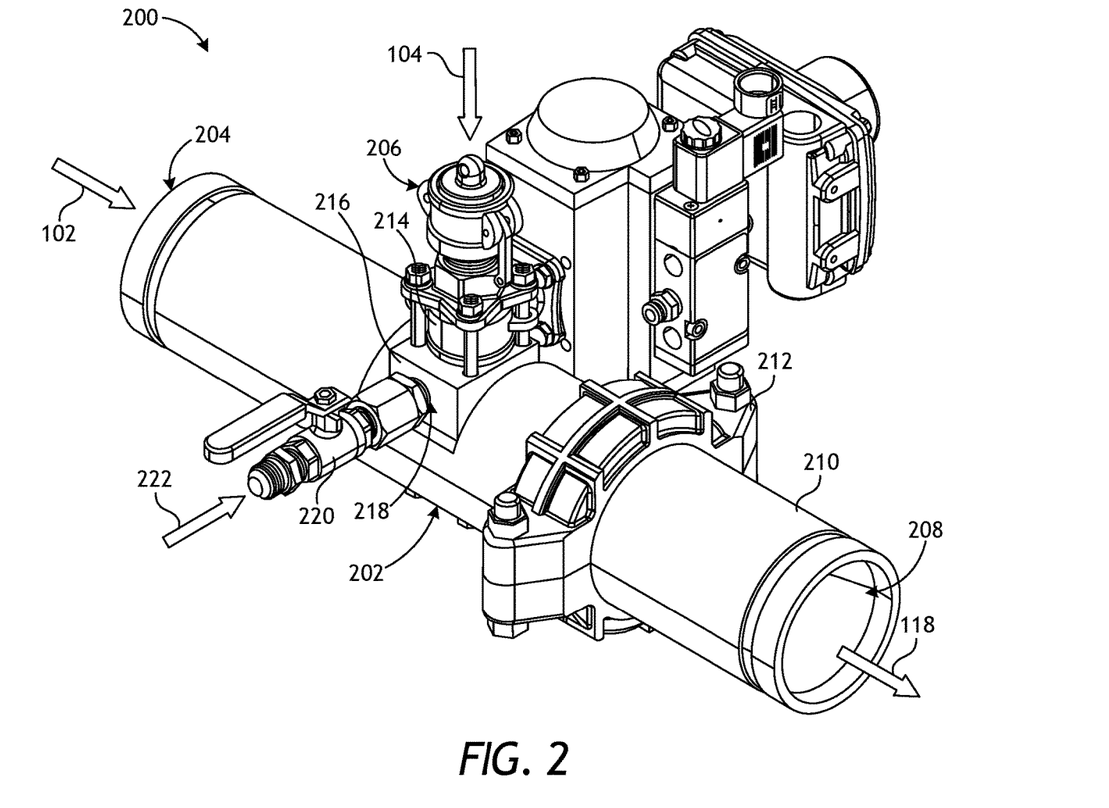
FIG. 2 is an isometric view of an example mixing device, according to one or more embodiments of the present disclosure.

As described above, the mixing device 106 includes an extender, which enables mixing the hydratable additive composition and the hydrating liquid composition in the extensional flow regime. By way of nonlimiting example, FIG. 2 is an isometric view of an example mixing device 200, according to one or more embodiments of the present disclosure. The mixing device 200 may be the same as or similar to the mixing device 106 of FIG. 1.

The hydrating liquid composition 102 may be introduced into the extender 202 via the fluid inlet 204, and the hydratable additive composition 104 (which can be a solid powder or in the form of a polymer slurry) may be introduced into the extender 202 via the additive inlet 206. As described above, the hydratable additive 104 may be fed into the additive inlet 206 either from the auger 112 (FIG. 1) or after being pre-wetted in the wetting container 114 (FIG. 1). The mixture 118 may exit the extender 202 via the outlet 208 to be conveyed into the hydration tank 120 (FIG. 1), as generally described above.

The geometry of the extender 202 may cause the hydrating liquid composition 102 to form a jet that flows through the extender 202 and generates a low-pressure vacuum that draws the hydratable additive 104 into the mixing device 106 to mix with the hydrating liquid composition 102. The formation of the jet also imparts energy to the mixture to help hydrate the hydratable additive 104.

In some embodiments, the outlet 208 may be formed by a diffuser 210 coupled to the extender 202 at a coupling 212. In other embodiments, however, the diffuser 210 may form an integral part or extension of the extender 202.

In some embodiments, the additive inlet 206 may include a valve 214 that regulates flow of the hydratable additive 104 into the extender 202. The valve 214 may comprise, for example, a ball valve that may be manually operated or operated by automation using the control system 128 (FIG. 1). In the illustrated embodiment, the additive inlet 206 may further include a spacer 216 interposing the valve 214 and the extender 202. The spacer 216 may define a flush port 218 and a flush valve 220 may be fluidly coupled to the spacer 216 at the flush port 216. The flush valve 220 may be actuated as needed to introduce a flushing fluid 222 into the extender 202 to remove any buildup of the hydratable additive 104 that may be coated on the inner walls of the spacer 216 and a suction port that feeds the hydratable additive 104 into the extender 202. Similar to the valve 214, the flush valve 220 may be manually operated or operated by automation using the control system 128 (FIG. 1).

When it is desired to flush the system, the valve 214 may be closed (either manually or automated), and the flush valve 220 may be opened (either manually or automated) to allow the flushing fluid 222 to enter the spacer 216 and the extender 202. The flushing fluid 222 may be any fluid that may sufficiently remove built-up hydratable additive 104 including, but not limited to, water (e.g., deionized, distilled, sterilized, etc.), a gas (e.g., air, nitrogen, carbon dioxide, etc.), an alcohol (e.g., ethanol, isopropanol, etc.), or any combination thereof. In at least one embodiment, the flushing fluid 222 may comprise a portion of the hydrating liquid composition 102 separated from the main portion and piped to the flush valve 220.

Figure 3:
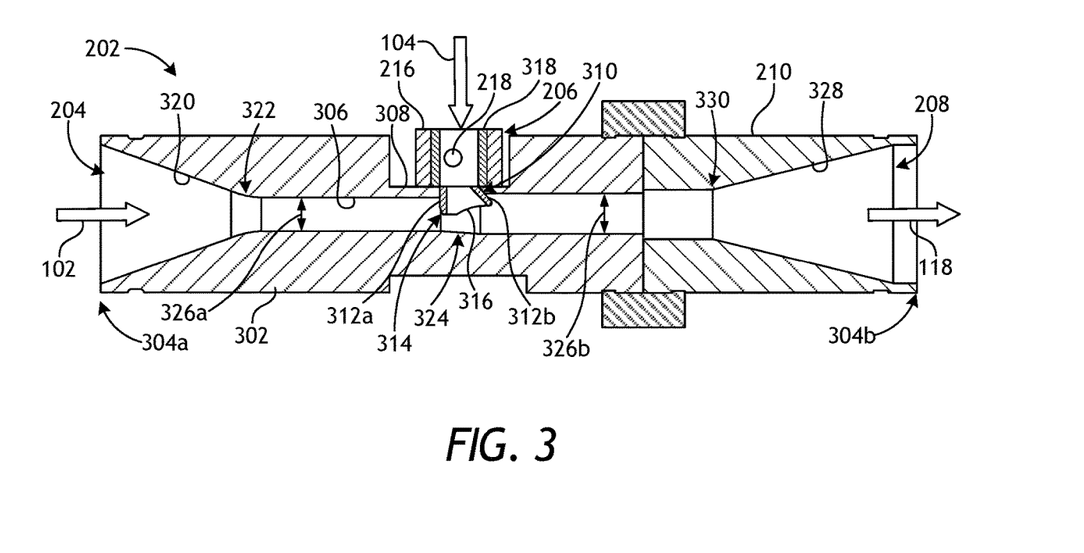
FIG. 3 is a cross-sectional side view of one embodiment of the extender of FIG. 2.

FIG. 3 is a cross-sectional side view of a nonlimiting embodiment of the extender 202. As illustrated, the extender 202 includes an elongate body 302 having a first end 304a and a second end 304b. The fluid inlet 204 is provided at the first end 304a, the outlet 208 is provided at the second end 304b, and a throat 306 extends between the fluid inlet 204 and the outlet 208. In some embodiments, the extender 202 may be made of a metal, such as carbon steel, stainless steel (e.g., polished stainless steel, chrome plated steel, etc.), aluminum, any alloys thereof, or any combination thereof. Alternatively, the extender 202 may be made of a plastic or polymer, such as polytetrafluoroethylene (PTFE or TEFLON®), NYLON®, HYLON®, polyvinyl chloride (PVC), chlorinated polyvinyl chloride (CPVC), or any combination thereof. In one or more embodiments, a hydrophobic coating may be applied to the inner walls of some or all of the extender 202. In yet other embodiments, the inner walls of some or all of the extender 202 may be polished to reduce friction.

Only a portion of the additive inlet 206 is depicted in FIG. 3. More particularly, the valve 214 (FIG. 2) is omitted, but the spacer 216 is depicted and defines the flush port 218 through which the flushing fluid 222 (FIG. 2) can be injected into the extender 202. In the illustrated embodiment, a recessed portion or "cutout" 308 is defined in the outer wall of the body 302, and the additive inlet 206 may be secured to the extender 202 within the cutout 308. Mounting the additive inlet 206 to the extender 202 within the cutout 308 helps to mitigate the occurrence of the hydratable additive 104 coating (covering) the inner walls of the additive inlet 206.

The additive inlet 206 may further include a suction port 310 that extends from the spacer 216 and into the throat 306 of the extender 202 at an intermediate point between the first and second ends 304a,b. The suction port 310 may be generally cylindrical and may expand or otherwise flare outward as it extends into the throat 306. In such embodiments, the diameter of the suction port 310 at or near the spacer 216 may be smaller than the diameter of the suction port 310 at its opposing end within the throat 306. This may prove advantageous in providing a larger discharge area for the hydratable additive 104 to be combined with the hydrating fluid 102 flowing through the throat 306.

In some embodiments, a leading (upstream) edge 312a of the suction port 310 may extend deeper (further) into the throat 306 as compared to a trailing (downstream) edge 312b of the suction port 310. This may prove advantageous in helping to prevent the incoming hydratable additive 104 from rebounding off the jet of hydrating fluid 102 flowing through the throat 306 and splashing back onto portions of the suction port 310. Moreover, in at least one embodiment, the leading edge 312a may define or provide a beveled bottom edge 314 and the suction port 310 may define a chamfered portion 316 that facilitates the transition between the leading and trailing edges 312a,b. The beveled bottom edge 314 and the chamfered portion 316 may be designed to help minimize or prevent splashing of the hydratable additive 104 as it is introduced into the throat 306.

In some embodiments, the suction port 310 may be made of a metal, such as carbon steel, stainless steel (e.g., polished stainless steel, chrome plated steel, etc.), aluminum, any alloys thereof, or any combination thereof. Alternatively, the suction port 310 may be made of a plastic or a polymer, such as polytetrafluoroethylene (PTFE or TEFLON®), NYLON®, HYLON®, polyvinyl chloride (PVC), chlorinated polyvinyl chloride (CPVC), or any combination thereof. In yet other embodiments, or in addition thereto, all or a portion of the spacer 216 and the suction port 310 may be lined with a lubricious material 318, such as CPVC. The lubricious material 318 may help repel the hydratable additive 104 and help facilitate a cleaner flushing when the flush port 218 is used to introduce the flushing fluid 222 (FIG. 2) to remove any buildup of the hydratable additive 104 that may be coated on the inner walls of the spacer 216 and the suction port 310. In at least one embodiment, the lubricious material 318 may further line the inner walls of the valve 214 (FIG. 2).

In embodiments that include flushing capabilities, the extender 202 may be cleaned and flushed at periodic intervals, such as at every 20 minutes of operation, or every 30 minutes, every hour, etc. In such embodiments, the control system 128 (FIG. 1) may autonomously control operation of the flushing operations. The control system 128 may also use various flow and pressure measurements to ensure that the extender 202 is maintaining suitable suction conditions. In the event any parameters deviate from normal values, the control system 128 may cause the valve 214 (FIG. 2) to close to eliminate a backflush condition through the suction line, and initiate a flush of the extender 202.

The extender 202 may also be flushed before and/or after the mixing process is completed. Flushing the extender 202 prior to starting a mixing process may prove advantageous since if there is any hydratable additive 104 already built up on the inner walls of the extender 202 (e.g., the valve 214 of FIG. 2, the spacer 216, and the suction port 310), it will have already absorbed water and softened, thus making it much easier to flush it as opposed to a fresh build-up of the hydratable additive 104. In some embodiments, the entire fluid pressure force of the mixing pump 108 (FIG. 1) may be used in the flushing process.

The throat 306 may form at least a portion of the elongated passageway described herein above that helps elongate and unfold the polymer structure of the hydratable additive 104 with minimum damage. Accordingly, the elongated passageway and the throat 306 may comprise the same structure and may be referred to herein interchangeably. More specifically, the geometry of the extender 202 may help ensure that the hydrating liquid composition 102 flowing through the throat 306 smoothly converges and mitigates splashing where the hydratable additive 104, especially dry hydratable additive 104, is introduced into the stream at the suction port 310. More particularly, the fluid inlet 204 may define or otherwise provide a converging portion 320 that tapers inward to form a nozzle. The hydrating liquid composition 102 forms a jet as it is forced to transition from the converging portion 310 to the throat 306.

In embodiments, the converging portion 320 may transition to the throat 306 at an arcuate transition 322 that exhibits a radius. As opposed to a sharp corner transition, the arcuate transition 322 provides smooth and curved transition walls. The radius and arcuate length of the arcuate transition 322 may be determined based on the remaining geometry of the extender 202. In at least one embodiment, the arcuate length of the arcuate transition 322 may be about 2.0 inches, but could alternatively be less than or greater than 2.0 inches, without departing from the scope of the disclosure. The arcuate transition 322 may help the flow of the hydrating liquid composition 102 to become extensional and smooth, with little or no turbulence, as it forms the jet flowing into the throat 306, and smoother flow of the hydrating liquid composition 102 may help prevent splashing as the hydratable additive 104 enters the throat 306 at the suction port 310.

During example operation, in some embodiments, opening of the valve 214 (FIG. 2) to introduce the hydratable additive 104 may be delayed for a short period (e.g., 5 or more seconds) to allow the flow of the hydrating fluid 102 through the throat 306 to become extensional. Once proper conditions are attained, the valve 214 can be opened to start feeding the hydratable additive 104 and forming the mixture 118.

In some embodiments, the diameter of the throat 306 may increase at or near the suction port 310 and otherwise where the hydratable additive 104 is introduced into the throat 306. More specifically, the throat 306 may define an expansion transition 324 that increases the diameter of the throat 306 in the downstream direction. Consequently, the diameter 326a of the throat 306 upstream from the expansion transition 324 may be smaller than the diameter 326b of the throat 306 downstream from the expansion transition 324. Increasing the diameter of the throat 306 at or near the suction port 310 may prove advantageous in removing the jet of hydrating fluid 102 from the walls of the throat 306 at that point so that it does not impinge directly on abrupt structural edges of the suction port 310. The expansion transition 324 also provides additional room for the hydratable additive 104 to be introduced into the throat 306.

The diffuser 210 extends the length of the throat 306 and provides or otherwise defines a diverging portion 328 that tapers outward in the downstream direction. The throat 306 may transition to the diverging portion 328 at a transition 330. In some embodiments, as illustrated, the transition 330 may provide a sharp corner transition. In other embodiments, however, the transition 330 may provide a smooth, curved transition across an arcuate portion having a radius, without departing from the scope of the disclosure.

Hydratable Additive

In some embodiments, the hydratable additive 104 may include dry polymers and polymer slurries including natural and derivatized hydratable polymers, such as polysaccharides, biopolymers, and other polymers. Hydratable additives include polymers that are approved from food, drug, and personal care use by any relevant governmental regulating agency, such as the USFDA. In some embodiments, hydratable additives are capable of generating viscosity at relavitely high alcohol levels, such as 50% or higher.

Examples of polymers that may be used include arabic gums, cellulose, karaya gums, xanthaii, tragacanth gums, ghatti gums, carrageenin, psyllium, acacia gums, tamarind gums, guar gums, locust bean gums, and the like. Modified gums, including carboxyalkyl derivatives, such as carboxymethyl guar and hydroxyalkyl derivatives such as hydroxypropyl guar (HPG), can also be employed. Doubly derivatized gums such as carboxymethyl hydroxypropyl guar (CMHPG) can also be used. Generally, carboxyalkyl guar, carboxyalkylhydroxyalkyl guar, and the like may be used, wherein the alkyl groups may comprise methyl, ethyl or propyl groups. In some embodiments, galactomanans such as guar, including natural, modified, or derivative galactomanans, may be used.

In some embodiments, the hydratable additive 104 may comprise a cellulose. Examples of celluloses, modified celluloses, and cellulose derivatives that may be used include cellulose, cellulose ethers, esters, and the like. Generally, any of the water-soluble cellulose ethers can be used. Those cellulose ethers include, among others, the various carboxyalkyl cellulose ethers, such as carboxyethyl cellulose and carboxymethyl cellulose (CMC); mixed ethers such as carboxyalkylethers, e.g., carboxymethyl hydroxyethyl cellulose (CMHEC); hydroxyalkyl celluloses, such as hydroxyethyl cellulose (HEC) and hydroxypropyl cellulose; alkyhydroxyalkyl celluloses, such as methylhydroxypropyl cellulose; alkyl celluloses, such as methyl cellulose, ethyl cellulose, and propyl cellulose; alkylcarboxyalkyl celluloses, such as ethylcarboxymethyl cellulose; alkylalkyl celluloses, such as methylethyl cellulose; hydroxyalkylalkyl celluloses such as hydroxypropylmethyl cellulose; and the like. Generally, carboxyalkyl cellulose, carboxyalkyl hydroxyalkyl cellulose and the like may be used, wherein the alkyl groups may comprise methyl, ethyl or propyl groups. In addition, derivatized celluloses, such as a hydroxyethyl cellulose grafted with vinyl phosphonic acid may be used.

In some embodiments, the hydratable additive 104 may comprise a hydratable synthetic polymer. Examples of hydratable synthetic polymers and copolymers that can be utilized include, but are not limited to, carbomers such as polyacrylate, polymethacrylate, acrylamide-acrylate copolymers, acrylamide homopolymers and copolymers (i.e., polyacrylamides), ammonium polyacrylolydimethyl taurate, maleic anhydride methylvinyl ether copolymers, polyvinyl lactams, polyvinyl acetates, methyl polyvinyl ethers, polystyrene, and polyacrylonitrile, and any combination thereof. In some embodiments, acidic polymers such as polyacrylates can also be used in conjunction with stabilizers and neutralizing compounds such as polyethoxylated amines, including ethoxylated (15) cocoa alkylamine, and other compounds approved for use in cosmetic compositions.

Polymeric hydratable additives may have a molecular weight of 10,000 g/mol to 50,000,000 g/mol or greater. However, the methods of the present disclosure are particularly useful at the higher molecular weights because such polymer are typically more difficult to hydrate and possibly more sensitive to high shear degradation. Some embodiments may utilize polymeric hydratable additives having a molecular weight of 500,000 g/mol to 50,000,000 g/mol, or 1,000,000 g/mol to 50,000,000 g/mol, or 5,000,000 g/mol to 50,000,000 g/mol, or 10,000,000 g/mol to 50,000,000 g/mol.

Humectant

Hydratable additives disclosed herein can be formulated with one or more humectants that prevent damage to the skin following application of a gelled sanitizer composition. Humectants can include glycerol/glycerin, derivatives thereof, sodium hyaluronate, hyaluronic acid, betaine, amino acids, glycosaminoglycans, honey, sorbitol, glycols such as propylene glycol, polyols, sugars, hydrogenated starch hydrolysates, pyrrolidonecarboxylic acids, lactic acid, lactates, urea, and the like.

Hydrating Liquid Composition

Hydrating liquid compositions disclosed herein include mixtures water and one or more solvents. The water component is free of microorganisms and includes water treated by any suitable purification process, including deionization, ozonation, filtration, and the like. Solvents can include C2-C10 alcohols and polyalcohol solvents such as ethanol, isopropanol, butanol, and the like. Hydrating liquid compositions can also include peroxides, humectants, and other cosmetically acceptable additives for personal products such as fragrances and coloring.

Peroxide

Hydrating fluid compositions disclosed herein can include one or more peroxides that function as an initial sanitizer to remove potential pathogens in the hydrating fluids used to formulate gelled sanitizer compositions. Peroxides disclosed herein include, for example, hydrogen peroxide, dicumyl peroxide, di-tert-butyl peroxide, t-butyl perbenzoate, benzoyl peroxide, cumene hydroperoxide, t-butyl peroctoate, methyl ethyl ketone peroxide, 2,5-dimethyl-2,5-di(t-butyl peroxy)hexane, lauryl peroxide, peracetates, and other compounds including a peroxy bond such as persulphates, perborates, percarbonates, perphosphates, and persilicates, and other oxidizers such as hypochlorites, Examples To facilitate a better understanding of the embodiments of the present invention, the following examples of preferred or representative embodiments are given. In no way should the following examples be read to limit, or to define, the scope of the invention.

Example 1: Comparative Gelled Sanitizer Preparation

In this example, a sanitizer is formulated according to a standard method in which a shear mixer is used to combine the formula components. A mixing vessel is charged with a combination of 140.45 g ethanol and 4.65 g isopropanol and sheared with an overhead mixer at 1,000 RPM. Next, a hydratable additive in the form of a polymer slurry was prepared from 0.5 g of Margel-EZ1 (from MAROON GROUP™) and 4 g of Ticacel (from TIC GUMS™), and mixing was continued for 5 minutes. The mixture was then diluted with 136 g of deionized water and mixed for 10 minutes; 10.85 of glycerol was added as a humectant and mixed for 1 minute; an additional 200.85 g of ethanol was added to reach the targeted alcohol concentration and mixed for 5 minutes; and 2.7 g of hydrogen peroxide was added to sanitize the mixture.

In the comparative mixing schedule, the total mix time required to make the product is 22 minutes. Of this total 68% (15 minutes) is tied directly to a process that is designed to hydrate the polymer to its peak viscosity while minimizing the amount of polymer that is either poorly mixed/hydrated or had formed "fisheyes".

Example 2: Representative Gelled Sanitizer Preparation

In the next example, a gelled sanitizer composition is prepared using a process in accordance with the present disclosure. The amounts and ratios of the components are provided in essentially the same quantities described with respect to Example 1. First, the ethanol, water, and peroxide are combined and mixed for a minute to produce a hydrating fluid composition. A hydratable additive mixture was then prepared by combining the polymer viscosifiers (95 wt % Margel-EZ1 and 5% Ticacel) to homogeneity by extender for 5 to 10 minutes, followed by addition of glycerol and continued mixing to yield a hydrated polymer slurry. Ethanol was then added to reach the targeted alcohol concentration and mixed for 5 minutes to produce the gelled sanitizer composition.

TABLE 2

| Compound | Percent Composition | Phase | density (g/cm$^3$) | Weight (g) |
| --- | --- | --- | --- | --- |
| Ethanol | | Liquid | 0.79 | 557.50 |
| Glycerol | | Liquid | 1.26 | 250.00 |
| MarGel EZ-1 Powder | 5.00% | Solid | 1.25 | 6.01 |
| Ticacel HV Powder | 95.00% | Solid | 1.25 | 114.14 |
| Total | | | | 927.65 |

This approach decreases the total mixing time from 22 minutes to a total of 11-16 minutes. In some embodiments, the process can incorporate an extender that allows batch or continuous production of fully gelled sanitizer in seconds, and decrease the total manufacture time to something on the order of 3-5 minutes (excluding time for premixing of additives prior to the production run).

Embodiments Listing

The present disclosure provides, among others, the following examples, each of which may be considered as optionally including any alternate example. Clause 1. A method of producing a gelled sanitizer composition, comprising: preparing a hydrating fluid composition comprising water and one or more selected from a group consisting of alcohol and peroxide; preparing a hydratable additive; and combining the hydrating fluid composition and the hydratable additive to produce a gelled composition.

Clause 2. The method of clause 1, wherein the hydratable additive comprises a humectant.

Clause 3. The method of clause 2, wherein the humectant is glycerol.

Clause 4. The method of clause 1, wherein the hydrating fluid composition comprises a C2-C10 alcohol.

Clause 5. The method of clause 1, wherein the hydrating fluid composition comprises a mixture of ethanol and isopropanol.

Clause 6. The method of clause 1, further comprising combining an alcohol with the gelled composition to produce a gelled sanitizer composition.

Clause 7. The method of clause 1, wherein combining the hydrating fluid composition and the hydratable additive comprises placing the the hydrating fluid composition and the hydratable additive in an extensional flow regime through an elongated passageway of an extender and a flow rate of the hydrating liquid composition and a diameter of the elongated passageway are sufficient to achieve a Reynolds number of 20,000 or greater.

Clause 8. A method, comprising: flowing a hydrating liquid composition in an extensional flow regime through an elongated passageway of an extender, wherein the hydrating liquid composition comprises water and a C2-C10 solvent, and a flow rate of the hydrating liquid composition and a diameter of the elongated passageway are sufficient to achieve a Reynolds number of 20,000 or greater; and adding a hydratable additive to the hydrating liquid composition in the elongated passageway to produce a mixture comprising the hydratable additive that is at least partially hydrated.

Clause 9. The method of clause 8, wherein the hydratable additive comprises a humectant.

Clause 10. The method of clause 8, further comprising prewetting the hydratable additive with a portion of the hydrating liquid composition before introduction of the hydratable additive to the elongated passageway.

Clause 11. The method of clause 8, wherein the flow rate of the hydrating liquid composition is at least 50 gallons per minute through the elongated passageway and the diameter of the elongated passageway is 45 mm or less.

Clause 12. The method of clause 8, wherein the hydratable additive is present in the gelled composition at a percent by weight (wt %) in a range of 0.2 wt % to 3 wt %.

Clause 13. The method of clause 8, wherein the hydratable additive comprises a powder polymer having a water content of 10 wt % or less.

Clause 14. The method of clause 8, wherein the hydratable additive comprises a polymer having a weight average molecular weight of 10,000 g/mol to 50,000,000 g/mol.

Clause 15. A gelled sanitizer composition comprising a hydratable additive that is at least substantially hydrated and a hydrating liquid composition comprising water and a C2-C10 solvent, wherein the gelled sanitizer composition is produced according to a method comprising: flowing the hydrating liquid composition in a extensional flow regime through an elongated passageway of an extender, wherein a flow rate of the hydrating liquid composition and a diameter of the elongated passageway are sufficient to achieve a Reynolds number of 20,000 or greater; and adding the hydratable additive to the hydrating liquid composition in the elongated passageway to produce a mixture comprising the hydratable additive that is at least partially hydrated.

Clause 16. The gelled sanitizer composition of clause 15, wherein the hydratable additive comprises a humectant.

Clause 17. The gelled sanitizer composition of clause 16, wherein the humectant is glycerol.

Clause 18. The gelled sanitizer composition of clause 15, wherein the hydrating fluid composition comprises a mixture of ethanol and isopropanol.

Clause 19. The gelled sanitizer composition of clause 15, wherein the composition is substantially free of partially hydrated polymer.

Clause 20. The gelled sanitizer composition of clause 15, wherein the hydrating fluid composition comprises a peroxide.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure.

The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A method of producing a gelled sanitizer composition, comprising:
   preparing a hydrating fluid composition comprising water and one or more selected from a group consisting of alcohol and peroxide;
   preparing a hydratable additive; and
   combining the hydrating fluid composition and the hydratable additive in an extensional flow regime through an elongated passageway of an extender and a flow rate of the hydrating liquid composition and a diameter of the elongated passageway are sufficient to achieve a Reynolds number of 20,000 or greater to produce a gelled composition.

2. The method of claim 1, wherein the hydratable additive further comprises a humectant.

3. The method of claim 2, wherein the humectant is glycerol.

4. The method of claim 1, wherein the hydrating fluid composition comprises a C2-C10 alcohol.

5. The method of claim 1, wherein the hydrating fluid composition comprises a mixture of ethanol and isopropanol.

6. The method of claim 1, further comprising combining an alcohol with the gelled composition to produce a gelled sanitizer composition.

7. A method, comprising:
   flowing a hydrating liquid composition in an extensional flow regime through an elongated passageway of an extender, wherein the hydrating liquid composition comprises water and a C2-C10 solvent, and a flow rate of the hydrating liquid composition and a diameter of the elongated passageway are sufficient to achieve a Reynolds number of 20,000 or greater; and
   adding a hydratable additive to the hydrating liquid composition in the elongated passageway to produce a mixture comprising the hydratable additive that is at least partially hydrated.

8. The method of claim 7, wherein the hydratable additive comprises a humectant.

9. The method of claim 7, further comprising prewetting the hydratable additive with a portion of the hydrating liquid composition before introduction of the hydratable additive to the elongated passageway.

10. The method of claim 7, wherein the flow rate of the hydrating liquid composition is at least 50 gallons per minute through the elongated passageway and the diameter of the elongated passageway is 45 mm or less.

11. The method of claim 7, wherein the hydratable additive is present in the gelled composition at a percent by weight (wt %) in a range of 0.2 wt % to 3 wt %.

12. The method of claim 7, wherein the hydratable additive comprises a powder polymer having a water content of 10 wt % or less.

13. The method of claim 7, wherein the hydratable additive comprises a polymer having a weight average molecular weight of 10,000 g/mol to 50,000,000 g/mol.

14. A gelled sanitizer composition comprising:
   a hydratable additive that is at least substantially hydrated, wherein the hydratable additive comprises a polymer and a humectant, wherein the humectant is glycerol and
   a hydrating liquid composition comprising water and a C2-C10 solvent,
   wherein the gelled sanitizer composition is produced according to a method comprising:
   flowing the hydrating liquid composition in a extensional flow regime through an elongated passageway of an extender, wherein a flow rate of the hydrating liquid composition and a diameter of the elongated passageway are sufficient to achieve a Reynolds number of 20,000 or greater; and
   adding the hydratable additive to the hydrating liquid composition in the elongated passageway to produce a mixture comprising the hydratable additive that is at least partially hydrated.

15. The gelled sanitizer composition of claim 14, wherein the hydrating fluid composition comprises a mixture of ethanol and isopropanol.

16. The gelled sanitizer composition of claim 14, wherein the composition is substantially free of partially hydrated polymer.

17. The gelled sanitizer composition of claim 14, wherein the hydrating fluid composition comprises a peroxide.

* * * * *